United States Patent [19]

Jenko et al.

[11] 4,304,929

[45] Dec. 8, 1981

[54] PROCESS FOR PREPARING 4-(N-HEXADECYLAMINO)-BENZOIC ACID

[75] Inventors: Branko Jenko, Ljubljana-Polje; Nataša Hafner-Milač, Ljubljana; Joža Habjan, Ljubljana; Anton Prosen, Ljubljana; Igor Langof, Ljubljana, all of Yugoslavia

[73] Assignee: LEK tovarna farmacevtskih in kemicnih izdelkov, n.sol.o., Ljubljana, Yugoslavia

[21] Appl. No.: 128,208

[22] Filed: Mar. 7, 1980

[30] Foreign Application Priority Data

Mar. 9, 1979 [YU] Yugoslavia ............................ 579/79

[51] Int. Cl.$^3$ ............................................. C07C 99/00
[52] U.S. Cl. ................................................... 562/458
[58] Field of Search ......................... 260/577; 562/458

[56] References Cited

U.S. PATENT DOCUMENTS 3,868,416 2/1975 Albright et al. ..................... 562/458
4,154,756 5/1979 Shepherd ............................ 260/577

OTHER PUBLICATIONS

Dehmlow, Angew. Chem., vol. 16, #8, pp. 493–505 (1977).
Patel, Chem. Abst., vol. 91, #39275x (1979).

*Primary Examiner*—Natalie Trousof
*Assistant Examiner*—James H. Reamer
*Attorney, Agent, or Firm*—Pollock, Vande Sande & Priddy

[57] ABSTRACT

Preparation of 4-(n-hexadecylamino)-benzoic acid or salt thereof employing as catalyst quaternary ammonium or phosphonium salt.

11 Claims, No Drawings

PROCESS FOR PREPARING 4-(N-HEXADECYLAMINO)-BENZOIC ACID

The present invention relates to an improved process for preparing 4-(n-hexadecylamino)-benzoic acid of the formula

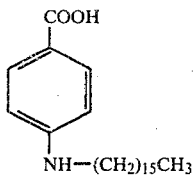

and physiologically acceptable salts thereof.

4-(n-hexadecylamino) benzoic acid is a substance possessing a substantial hypolipidemic activity and is used in medicine as an agent for reducing the increased phospholipide and/or triglyceride contents in blood. The increased contents of the mentioned substances cause numerous diseases, e.g. arteriosclerosis. For the pharmaceutical use, 4-(n-hexadecylamino)-benzoic acid is preferably converted into its sodium salt.

4-(n-hexadecylamino)-benzoic acid was described for the first time in the U.S. Pat. No. 3,868,416. The process for the synthesis thereof was performed by means of alkylating the nitrogen atom in 4-amino-benzoic acid with 1-bromohexadecane in a suitable solvent (e.g. ethanol), at 50°–150° C. and in the presence of an equivalent quantity of a base (e.g. KOH). The reaction took more than 48 hours and did not yield over 29.6% of 4-(n-hexadecylamino)-benzoic acid.

The object of the present invention is a novel process for the synthesis of 4-(n-hexadecylamino)-benzoic acid, which is performed by means of alkylating the nitrogen atom in 4-aminobenzoic acid with 1-bromohexadecane in the presence of quaternary ammonium salt or phosphonium salt catalysts of the formula: $[R_3 Q^+ Y]CL^-$. R is preferably ethyl, butyl, or caprilyl, Q is nitrogen or phosphorus, and Y is preferably methyl, benzyl or hexadecyl. These catalysts are nowadays known as "phase transfer" catalysts.

It has been established that the process according to the cited U.S. Pat. No. 3,868,416 gives poor results owing to the formation of substantial quantities of by-products as the alkylation with 1-bromohexadecane happens to yield by-products, alkylated on the oxygen atom of the carboxyl group. We have surprisingly found that—as far as we are aware of—the alkylation of aminobezoic acids and similar systems in the presence of "phase transfer" catalysts has not been described as yet. Under these conditions and in the presence of phase transfer catalysts, the duration of the reaction and the quantity of by-products are considerably reduced, whereas the yields of the 4-(n-hexadecylamino)-benzoic acid and the salts thereof are considerably increased. The preferred catalyst for the present reaction is tricaprilylmethylammonium chloride (Aliquat 336).

The process according to the invention is performed in accordance with the following reaction scheme:

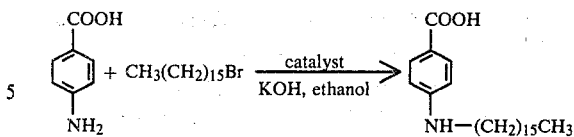

The process is illustrated, but in no way limited by the following Examples.

EXAMPLE 1

A mixture of 6.85 g of 4-aminobenzoic acid, 3.3 g of KOH, 17.6 ml of 1-bromohexane and 1.18 g of tricaprilylmethylammonium chloride (Aliquat 336) in 75 ml of ethanol (96%) was stirred at reflux temperature for 11 hours, whereupon there was added a solution of 5.6 g of KOH in 50 ml of ethanol (50%) and the stirring was continued for 3 hours at reflux temperature. To the hot solution there were added 20 ml of conc. HCl, whereupon it was cooled down, the precipitated product was separated on a suction filter, washed with 50 ml of water and dried in vacuo at 50° C. The product was transferred into a distillation apparatus and the excess of 1-bromohexadecane and 1-hexadecanol, which was formed during the reaction, was distilled of at 70°–110° C. and 0.02–0.1 mm Hg. The residue was crystallized from benzene and there were obtained 8.62 g (47.8%) of 4-(n-hexadecylamino)-benzoic acid, m.p. 104°–107° C. and complete m.p. 122°–126° C. If desired, it can be converted into its sodium salt in a usual manner.

EXAMPLE 2

A mixture of 13.7 g of 4-aminobenzoic acid, 6.6 g of KOH, 35.2 ml of 1-bromohexadecane and 1.6 g of benzyltriethylammonium chloride (TEBA) in 150 ml of ethanol (96%) was stirred for 12 hours at reflux temperature, thereupon there was added a solution of 11.2 g of KOH in 100 ml of ethanol (50%) and the stirring was continued for 3 hours at reflux temperature. To the hot solution there were added 40 ml of conc. HCl, whereupon it was cooled down, the precipitated product was separated on a suction filter and subsequently washed with 100 ml of water and dried in vacuo at 50° C. The crude product was crystallized from benzene.

There were obtained 11.2 g (31%) of 4-(n-hexadecylamino)-benzoic acid, m.p. 104°–107° C., complete m.p. 122°–126° C.

EXAMPLE 3

27.4 g (0.2 mol) of 4-aminobenzoic acid, 11.2 g of KOH, 64 g (0.21 mol) of 1-bromohexadecane and 4.64 g (10 mmol) of hexadecyltributylphosphonium chloride were suspended in 250 ml of ethanol (96%) and the reaction mixture was stirred for 12 hours at reflux temperature. While the solution was still hot, there were added, drop by drop, 80 ml of conc. HCl and the reaction mixture was left to cool down to ambient temperature. Thereupon the precipitated product was separated on a suction filter, washed with water and dried. After the crystallization of the crude product from benzene, there was obtained the 4-(n-hexadecylamino)-benzoic acid, m.p. 107°–107° C., complete m.p. 122°–126° C., which could be optionally converted into its sodium salt.

What is claimed is:

1. In a process for the preparation of 4-(n-hexadecylamino)-benzoic acid and physiologically acceptable salts thereof by means of reacting 4-aminobenzoic acid and 1-bromohexadecane in the presence of a lower alkanol as solvent and in the presence of KOH the improvement which comprises carrying out the alkylation in the presence of a quaternary ammonium or phosphonium salt catalyst of the formula: $[R_3 Q^+ Y]Cl^-$ wherein R is ethyl, butyl or caprilyl; Y is methyl, benzyl or hexadecyl, and Q is nitrogen or phosphorus.

2. The process of claim 1 wherein said catalyst is tricaprilylmethylammonium chloride.

3. The process of claim 1 or 2 wherein said solvent is ethanol.

4. The process of claim 1 or 2 wherein the reaction is performed within 15 hours.

5. The process of claim 9 wherein the reaction is performed in 11 to 12 hours.

6. The process of claim 1 or 2 wherein the reaction is carried out at reflux.

7. The process of claim 1 wherein the reaction is carried out at 50°–150° C.

8. The process of claim 1 or 2 wherein said solvent is ethanol, the reaction is performed within 15 hours, and the reaction is carried out at reflux.

9. The process of claim 1 wherein the 4-(n-hexadecylamino)-benzoic acid is converted into a physiologically acceptable salt thereof.

10. The process of claim 1 wherein said catalyst is benzyltriethylammonium chloride.

11. The process of claim 1 wherein said catalyst if hexadecyltributylphosphonium chloride.

* * * * *